United States Patent
Nakatsuka et al.

(10) Patent No.: US 9,511,005 B2
(45) Date of Patent: Dec. 6, 2016

(54) DENTAL CURABLE COMPOSITION CONTAINING PARTICLES WITH DIFFERENT REFRACTIVE INDEXES

(71) Applicant: SHOFU INC., Kyoto-shi, Kyoto (JP)

(72) Inventors: Toshiyuki Nakatsuka, Kyoto (JP); Kazuya Shinno, Kyoto (JP); Satoshi Fujiwara, Kyoto (JP); Daisuke Hara, Kyoto (JP)

(73) Assignee: SHOFU INC., Kyoto-Shi (JP)

( * ) Notice: Subject to any disclaimer, the term of this patent is extended or adjusted under 35 U.S.C. 154(b) by 146 days.

(21) Appl. No.: 14/224,191

(22) Filed: Mar. 25, 2014

(65) Prior Publication Data

US 2015/0094396 A1 Apr. 2, 2015

(30) Foreign Application Priority Data

Sep. 30, 2013 (JP) .................. 2013-205696

(51) Int. Cl.
*A61K 6/083* (2006.01)
*A61K 6/00* (2006.01)

(52) U.S. Cl.
CPC ............. *A61K 6/083* (2013.01); *A61K 6/0005* (2013.01); *A61K 6/007* (2013.01); *A61K 6/0008* (2013.01); *A61K 6/0023* (2013.01); *A61K 6/0091* (2013.01)

(58) Field of Classification Search
CPC ........................... A61K 6/0005; A61K 6/083
See application file for complete search history.

(56) References Cited

U.S. PATENT DOCUMENTS

| | | | |
|---|---|---|---|
| 5,962,550 A | 10/1999 | Akahane et al. | |
| 6,300,389 B1* | 10/2001 | Sato | A61K 6/0005 106/36 |
| 2003/0036582 A1* | 2/2003 | Yamakawa | A61K 6/0073 523/115 |
| 2008/0319104 A1 | 12/2008 | Klapdohr et al. | |
| 2009/0299006 A1 | 12/2009 | Shinno et al. | |
| 2010/0216096 A1 | 8/2010 | Suzuki et al. | |
| 2013/0030081 A1 | 1/2013 | Tsujimoto et al. | |
| 2014/0206792 A1* | 7/2014 | Ishizaka | A61K 6/0005 523/115 |

FOREIGN PATENT DOCUMENTS

| | | | |
|---|---|---|---|
| CA | 2051333 | 3/1992 | |
| JP | 63-303906 | 12/1988 | |
| JP | 01-186807 | 7/1989 | |
| JP | 10-265318 | 10/1998 | |
| JP | 2006-131621 | 5/2006 | |
| JP | 2006-219439 | 8/2006 | |
| JP | 2007-532518 | 11/2007 | |
| JP | 2010-037324 | 2/2010 | |
| JP | 2010-215597 | 9/2010 | |
| JP | 5004952 | 8/2012 | |
| JP | WO 2012176877 A1 * | 12/2012 | ........... A61K 6/0005 |
| WO | 2005/097043 | 10/2005 | |

OTHER PUBLICATIONS

European Search Report dated Jun. 11, 2015, 9 pages.

* cited by examiner

*Primary Examiner* — Michael Pepitone
(74) *Attorney, Agent, or Firm* — Rankin, Hill & Clark LLP

(57) ABSTRACT

A single-paste, self-adhesive dental curable composition that has strong self-adhesion to biological hard tissues (such as enamel and dentin of teeth) and good color tone adaptability suitable for use for aesthetic restoration is provided. A dental curable composition contains: an inorganic particle (A) with an average grain size in the range of 0.1 to 50 μm; an inorganic particle (B) with an average grain size in the range of 0.1 to 50 μm; a polymerizable monomer (C); and a polymerization catalyst (D). The refractive index na of the inorganic particle (A) and the refractive index nb of the inorganic particle (B) meet the relationship of na>nb. A cured resin material (E), which is obtained by curing a polymerizable composition containing the polymerizable monomer (C) and the polymerization catalyst (D), has a refractive index ne that meets the relationship (1):

$$0 \le |na-ne| < 0.01 \le ne-nb \le 0.05 \qquad (1).$$

4 Claims, No Drawings

DENTAL CURABLE COMPOSITION CONTAINING PARTICLES WITH DIFFERENT REFRACTIVE INDEXES

CROSS-REFERENCE TO RELATED APPLICATIONS

This application claims foreign priority benefits under 35 U.S.C. §119(a)-(d) to JP 2013-205696 filed Sep. 30, 2013, which is hereby incorporated by reference in its entirety.

TECHNICAL FIELD

The present invention relates to a dental curable composition for use in the dental field such as a dental crown material, a filling material, a prosthetic material, and an adhesive material, and more particularly to a dental curable composition having stable adhesion to biological hard tissues (such as enamel and dentin of teeth) and having good color tone adaptability to the natural teeth.

BACKGROUND ART

In dental clinics, composite resin restoration in which a caries caused in a tooth is removed to form a cavity to be thereafter filled with a resin-based filling/restoring material is widely used. The composite resin restoration is characterized by reproducing an aesthetic state similar to that of the natural teeth and allowing a treatment to be completed with only one dental visit to reduce a burden on the patient. In order to achieve aesthetic restoration, it is important to match the color tone and the transparency of the resin-based filling/restoring material with those of teeth. The teeth have a high transparency and a light color tone at incisal ends, but have a low transparency and a dark color tone at neck portions and root portions. In order to aesthetically restore, using the resin-based filling/restoring material, various portions of the teeth with different transparencies and color tones as mentioned above, it is necessary to appropriately control the color tone and the transparency of the resin-based filling/restoring material. In general, the color tone and the transparency of the resin-based filling/restoring material are controlled by adjusting the amount of an additive such as a pigment contained in the resin-based filling/restoring material. For example, Patent Document 1 proposes an adjustment method in which a composite resin is caused to express translucency using an opalescent filler.

The resin-based filling/restoring material itself is not adhesive to teeth. Therefore, restoration with the material inevitably requires application of a dental adhesion system. The dental adhesion system acts on the enamel and the dentin of the teeth to be interposed between the resin-based filling/restoring material and the teeth to stably bond the material and the teeth to each other. Two types of dental adhesion systems are currently available in the market: one (a total-etching dental adhesion system) involves an etching process in which a phosphoric acid is used as a pre-treatment for the teeth, and the other (a self-etching dental adhesion system) involves a self-etching process for the teeth in which a tooth substance primer containing a polymerizable monomer having an acidic group is used and no water washing is required.

In order to make the resin-based filling/restoration further more convenient, there are proposed various related technologies in which the operative method of the dental adhesion system is further simplified. Patent Document 2 discloses a technology (an all-in-one, self-etching dental adhesion system) in which the tooth substance can be treated with a one-step operation using an adhesive in a single package without the need for a pre-treatment performed using a pre-treatment agent such as an etching agent, a conditioner, and a primer. Further, Patent Documents 3 to 5 propose technologies in which the cavity is filled with the resin-based filling/restoring material and the resin-based filling/restoring material is cured by one step of visible light irradiation in total with no substantial visible light irradiation performed after an adhesive is applied to the surface of the cavity. However, the resin-based filling/restoring material itself is not adhesive, and a dental adhesion system is required to bond the resin-based filling/restoring material to the cavity.

Meanwhile, dental treatments in which a glass ionomer cement that is adhesive to the tooth substance is used for filling/restoration or to seal pits and fissures are also widely performed. For the glass ionomer cement, basic glass which is a powder material is eroded by a liquid material which is an aqueous solution of an acid, and calcium ions and aluminum ions which are eluted during the erosion and carboxyl groups which are lateral groups of a polycarboxylic acid contained in the liquid material are subjected to chelate bonding and cured. Further, such ions are also subjected to chelate bonding with the tooth substance. Thus, the glass ionomer cement adheres to the tooth substance. The glass ionomer cement slightly stimulates the dental pulp, and thus can be said to be a highly biocompatible material. In addition, the material is self-adhesive to the tooth substance, and thus is widely used as a filling/restoring material (a glass ionomer-based filling/restoring material) as well as an adhesive material. The glass ionomer cement is advantageously characterized by persistently gradually releasing a minute amount of fluorine ions, and also used as a preventive material because it has a preventive effect, for example, suppressing or preventing a secondary caries and strengthening the tooth substance. In recent years, as described in Patent Document 6, there has been developed a material that has the respective characteristics of the resin-based filling/restoring material and the glass ionomer cement. Such material, however, still has the following defects: the material is low in physical properties and aesthetics compared to the resin-based filling/restoring material, and disadvantageously complicated in terms of the operative method because the material requires the concurrent use of the dental adhesion system and the pre-treatment agent.

RELATED-ART DOCUMENTS

Patent Documents

Patent Document 1: JP 2007-532518 A
Patent Document 2: JP 5004952 B2
Patent Document 3: JP 2006-131621 A
Patent Document 4: JP 2010-37324 A
Patent Document 5: JP 2010-215597 A
Patent Document 6: JP 10-265318 A.

SUMMARY OF INVENTION

Therefore, there is desired a resin-based filling/restoring material having self-adhesion to the tooth substance, without the need for a pre-treatment to be performed using an adhesion system or the like, in addition to maintaining high physical properties and good aesthetics of the resin-based filling/restoring material.

In view of the foregoing, it is an object of the present invention to provide a dental curable composition for use in the dental field such as a dental crown material, a filling material, a prosthetic material, and an adhesive material that has strong self-adhesion to biological hard tissues (such as enamel and dentin of teeth) and good color tone adaptability suitable for aesthetic restoration.

In order to address the foregoing issue, the inventors made diligent studies, and finally achieved the object by providing a dental curable composition containing two types of inorganic particles having a specific refractive index and a specific average grain size, a polymerizable monomer, and a polymerization catalyst. The present invention has been made based on the above finding. That is, the inventors provide the following dental curable composition in the present invention.

The present invention provides a dental curable composition containing: an inorganic particle (A) with an average grain size in the range of 0.1 to 50 μm and a refractive index na; an inorganic particle (B) with an average grain size in the range of 0.1 to 50 nm and a refractive index nb; a polymerizable monomer (C); and a polymerization catalyst (D). The refractive index na of the inorganic particle (A) and the refractive index nb of the inorganic particle (B) meet the relationship of na>nb. In the dental curable composition according to the present invention, in particular, a cured resin material (E), which is obtained by curing a polymerizable composition containing the polymerizable monomer (C) and the polymerization catalyst (D), has a refractive index ne that meets the relationship (1):

$$0 \leq |na-ne| < 0.01 \leq ne-nb \leq 0.05 \quad (1)$$

For example, the polymerizable monomer (C) may contain an acidic group-containing polymerizable monomer (F) and a non-acidic group-containing polymerizable monomer (G).

In this case, the polymerizable monomer (C) preferably contains the acidic group-containing polymerizable monomer (F) and the non-acidic group-containing polymerizable monomer (G) by a weight ratio of 3:97 to 50:50.

The non-acidic group-containing polymerizable monomer (G) may contain a hydrophilic polymerizable monomer (H) as a part thereof.

In this case, the hydrophilic polymerizable monomer (H) preferably accounts for 5 to 70% by weight of the total of the non-acidic group-containing polymerizable monomer (G).

EFFECT OF INVENTION

The present invention described above achieves the following effects. The dental curable composition according to the present invention is self-adhesive to biological hard tissues (such as enamel and dentin of teeth), and thus can be subjected to a convenient restorative procedure without the need for a tooth surface treatment which has conventionally been clinically performed. This makes it possible to shorten the procedure time, reduce a burden on both the operator and the patient, and reduce operational technical errors because of simplified operating steps. Further, the dental curable composition according to the present invention can have color tone adaptability that makes it possible to moderately screen the color of a background such as a cavity wall because of the relationship between the respective refractive indexes of the inorganic particles and the cured resin material, and that makes the dental curable composition less susceptible to the background color.

DETAILED DESCRIPTION OF PREFERRED EMBODIMENTS

The present invention will be described in detail below. The dental curable composition according to the present invention is characterized by the combined use of two types of inorganic particles (A) and (B) with an average grain size in the range of 0.1 to 50 μm, wherein the refractive index na of the inorganic particle (A) and the refractive index nb of the inorganic particle (B) meet the relationship of na>nb.

The inorganic particle (A) and the inorganic particle (B) that can be used for the dental curable composition according to the present invention may be any type of inorganic particle without restriction as long as the average grain size is in the range discussed earlier and the respective refractive indexes meet the relationship discussed earlier. The grain shape of the inorganic particles is not specifically limited, and may be any shape without restriction such as a spherical shape, a needle shape, tabular shape, a fracture shape, and a scale shape.

Specific examples of inorganic particles (A) and inorganic particles (B) which can be used for a curable dental composition according to the present invention include aluminium oxide, calcium carbonate, calcium sulfate, calcium hydroxide, barium sulfate, barium carbonate, strontium carbonate, talc, kaoline, clay, mica, hydroxyapatite, barium fluoride, calcium fluoride, strontium fluoride, silica, quartz, various glass (heavy metal such as sodium, strontium, barium, and lanthanum and/or glasses including fluorine, for example, aluminosilicate glass, borosilicate, aluminoborates, and boroaluminosilicate glass). Among these, strontium, barium, lanthanum, zirconium, titanium, silica, glass or the like are preferable, and zirconium, silica, aluminosilicate glass boroaluminosilicate glass are more preferable.

The average grain size of the inorganic particle (A) and the inorganic particle (B) is in the range of 0.1 to 50 μm, preferably in the range of 0.1 to 10 μm, and more preferably in the range of 0.1 to 5.0 μm. If the average grain size of the inorganic particle is less than 0.1 μm, the surface area of the filler per unit weight is so large that the amount of the filler to be compounded in the dental curable composition invention may not be increased, which may not result in expression of a sufficient mechanical strength. If the average grain size of the inorganic particle is more than 50 μm, on the other hand, the inorganic particle is subjected to settling or phase separation in the dental curable composition, thereby failing to attain stable performance.

The range of the refractive index na of the inorganic particle (A) and the refractive index nb of the inorganic particle (B) is not specifically limited as long as the relationship of na>nb is met. In consideration of the refractive index of polymerizable monomers suitably used in the dental field, however, the refractive index of the inorganic particle (A) and the inorganic particle (B) is preferably in the range of 1.40 to 1.70.

It should be noted, however, that the respective refractive indexes na and nb of the inorganic particle (A) and the inorganic particle (B) meet the following relationship (2) with the refractive index ne of a cured resin material (E), which is obtained by curing a polymerizable composition containing a polymerizable monomer (C) and a polymerization catalyst (D):

$$0 \leq |na-ne| < 0.01 \leq ne-nb \leq 0.05 \quad (2)$$

If the refractive indexes na, nb, and ne do not meet the above relationship, a significant deviation occurs in transparency between the dental curable composition and the natural teeth. If the transparency of the dental curable composition is too low compared to that of the natural teeth, an aesthetic state similar to that of the natural teeth may not be reproduced. In addition, the low transparency does not allow transmission of light, and therefore the polymerizability may be reduced inside the dental curable composition, which may result in problems in adhesion to the tooth substance and mechanical strength. If the transparency of the dental curable composition is too high compared to that of the natural teeth, on the other hand, the dental curable composition may be so susceptible to the background color that intended color tone adaptability may not be obtained.

It is also preferable to treat the surfaces of the inorganic particle (A) and the inorganic particle (B) by a surface treatment method using a surface treatment agent or the like in order to increase the functionality of the inorganic particles. Such surface-treated inorganic particles may also be used without restriction for the dental curable composition according to the present invention. In this case, it is only necessary that the refractive indexes of the inorganic particle (A) and the inorganic particle (B) before the surface treatment method is applied to increase the functionality of the inorganic particles should meet the relationship (2).

Specific examples of the surface treatment agent used to increase the functionality of the surfaces of the inorganic particles (A) and (B) include a surfactant, fatty acid, organic acid, inorganic acid, a silane coupling agent, a titanate coupling agent, and polysiloxane. Specific examples of the surface treatment method include a method in which the surface treatment agent is sprayed from above the filler in a fluidized state, a method in which the filler is dispersed in a solution containing the surface treatment agent, and a method in which several types of surface treatment agents are applied in layers to the surface of the filler. However, the surface treatment agent and the surface treatment method are not limited thereto. Such surface treatment agents and surface treatment methods may be used singly or in various combinations, respectively.

If three or more types of inorganic particles are compounded in the dental curable composition according to the present invention, the effect of the present invention can be achieved if two of the compounded inorganic particles selected as desired are defined as the inorganic particle (A) and the inorganic particle (B), the average grain size of the inorganic particle (A) and the inorganic particle (B) is in the range of 0.1 to 50 μm, the refractive index na of the inorganic particle (A) and the refractive index nb of the inorganic particle (B) meet the relationship of na>nb, and the relationship (2) is met.

The polymerizable monomer (C) is not limited to a specific type, and may include an acidic group-containing polymerizable monomer (F), a non-acidic group-containing polymerizable monomer (G), or both thereof.

The dental curable composition according to the present invention is characterized by containing the acidic group-containing polymerizable monomer (F) as the polymerizable monomer (C). This allows interaction with biological hard tissues (such as enamel and dentin of the natural teeth) as an adherend to express adhesion to biological hard tissues.

The acidic group-containing polymerizable monomer (F) that can be used for the dental curable composition according to the present invention may be any polymerizable monomer having an acidic group without restriction. Specific examples of the acidic group of the acidic group-containing polymerizable monomer (F) include, but are not limited to, a phosphate group, a pyrophosphate group, a phosphonate group, a carboxylate group, a sulfonate group, and a thiophosphate group. The number and the type of radical-polymerizable unsaturated groups (monofunctional groups or polyfunctional groups) of the acidic group-containing polymerizable monomer (F) are not limited in any way. Specific examples of the unsaturated groups of the acidic group-containing polymerizable monomer (F) include an acryloyl group, a methacryloyl group, a styryl group, a vinyl group, and an allyl group. The acidic group-containing polymerizable monomer preferably has an acryloyl group and/or a methacryloyl group among these unsaturated groups.

The acidic group-containing polymerizable monomer (F) may also contain in its molecule other functional groups such as an alkyl group, a halogen groups, an amino group, a glycidyl group, and a hydroxyl group. The acidic group-containing polymerizable monomer (F) may not only be a monomer with a short main chain but also be an oligomer, a prepolymer, or the like with a long main chain. Further, derivatives of the acidic group-containing polymerizable monomer (F) such as a metallic salt, an ammonium salt, and an acid chloride obtained by partially neutralizing the acidic group of the acidic group-containing polymerizable monomer (F) may also be used to the extent that the adhesion to various adherends is not adversely affected.

Specific examples of the acidic group-containing polymerizable monomer (F) that can be used for the dental curable composition according to the present invention are as follows. Herein, the terms "(meth)acrylates" and "(meth)acryloyls" are used to comprehensively express both acryloyl group-containing polymerizable monomers and methacryloyl group-containing polymerizable monomers, respectively.

Example of acidic group-containing polymerizable monomers having a phosphate group include, but are not limited to acidic group-containing polymerizable monomers such as (meth)acryloyloxymethyldihydrogenphosphate, 2-(meth)acryloyloxyethyldihydrogenphosphate, 3-(meth)acryloyloxypropyldihydrogenphosphate, 4-(meth)acryloyloxybutyldihydrogenphosphate, 5-(meth)acryloyloxypentyldihydrogenphosphate, 6-(meth)acryloyloxyhexyldihydrogenphosphate, 7-(meth)acryloyloxyheptyldihydrogenphosphate, 8-(meth)acryloyloxyoctyldihydrogenphosphate, 9-(meth)acryloyloxynonyldihydrogenphosphate, 10-(meth)acryloyloxydecyldihydrogenphosphate, 11-(meth)acryloyloxyundecyldihydrogenphosphate, 12-(meth)acryloyloxydodecyldihydrogenphosphate, 16-(meth)acryloyloxyhexadecyldihydrogenphosphate, 20-(meth)acryloyloxyeicosyldihydrogenphosphate, di(meth)acryloyloxyethylhydrogenphosphate, di(meth)acryloyloxybutylhydrogenphosphate, di(meth)acryloyloxyhexylhydrogenphosphate, di(meth)acryloyloxyoctylhydrogenphosphate, di(meth)acryloyloxynonylhydrogenphosphate, di(meth)acryloyloxydecylhydrogenphosphate, 1,3-di(meth)acryloyloxypropyl-2-dihydrogenphosphate, 2-(meth)acryloyloxyethylphenylhydrogenphosphate 2-(meth)acryloyloxyethyl-2'-bromoethylhydrogenphosphate, and (meth)acryloyloxyethylphenylphosphate.

Example of acidic group-containing polymerizable monomers having a pyrophosphate group include, but are not limited to acidic group-containing polymerizable monomers such as di[2-(meth)acryloyloxyethyl]pyrophosphate, di[3-(meth)acryloyloxypropyl]pyrophosphate, di[4-(meth)acryloyloxybutyl]pyrophosphate, di[5-(meth)acryloyloxypentyl]pyrophosphate, di[6-(meth)acryloyloxyhexyl]pyrophosphate, di[7-(meth)acryloyloxyheptyl]pyrophosphate, di[8-(meth)acryloyloxyoctyl]pyrophosphate, di[9-(meth)acryloyloxynonyl]pyrophosphate, di[10-(meth)acryloyloxydecyl]pyrophosphate, di[12-(meth)acryloyloxydodecyl]pyrophosphate, tetra[2-(meth)acryloyloxyethyl]pyrophosphate, and tri[2-(meth)acryloyloxyethyl]pyrophosphate.

Example of acidic group-containing polymerizable monomers having a carboxylate group include, but are not limited to acidic group-containing polymerizable monomers such as (meth)acrylate, 2-chloro(meth)acrylate, 3-chloro(meth)acrylate, 2-cyano(meth)acrylate, aconitic acid, mesaconic acid, maleic acid, maleic anhydride, itaconic acid, itaconic anhydride, fumaric acid, glutaconic acid, citraconic acid, utraconic acid, 1,4-di(meth)acryloyloxyethylpyromellitate, 6-(meth)acryloyloxynaphthalene-1,2,6-tricarboxylate, 1-butene-1,2,4-tricarboxylate, 3-butene-1,2,3-tricarboxylate, N-(meth)acryloyl-p-aminobenzoate, N-(meth)acryloyl-5-aminosalycilate, 4-(meth)acryloyloxyethyltrimellitate and anhydride thereof, 4-(meth)acryloyloxybutyltrimellitate and anhydride thereof, 2-(meth)acryloyloxybenzoate, β-(meth)acryloyloxyethylhydrogensuccinate, β-(meth)acryloyloxyethylhydrogenmaleate, 11-(meth)acryloyloxy-1,1-undecanedicarboxylate, p-vinylbenzoate, 4-(meth)acryloyloxyethoxycarbonylphthalate, 4-(meth)acryloyloxybutyloxycarbonylphthalate, 4-(meth)acryloyloxyhexyloxycarbonylphthalate, 4-(meth)acryloyloxyoctyloxycarbonylphthalate, 4-(meth)acryloyloxydecyloxycarbonylphthalate and anhydride thereof, 5-(meth)acryloylaminopentylcarboxylate, 6-(meth)acryloyloxy-1,1-hexandicarboxylate, 8-(meth)acryloyloxy-1,1-octanedicarboxylate, 10-(meth)acryloyloxy-1,1-decanedicarboxylate, and 11-(meth)acryloyloxy-1,1-undecanedicarboxylate.

Example of acidic group-containing polymerizable monomers having a phosphonate group include, but are not limited to, acidic group-containing polymerizable monomers such as 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, and 10-(meth)acryloyloxydecyl-3-phosphonoacetate.

Example of acidic group-containing polymerizable monomers having a sulfonate group include, but are not limited to, acidic group-containing polymerizable monomers such as 2-(meth)acrylamido-2-methylpropanesulfonate, styrenesulfonate, 2-sulfoethyl(meth)acrylate, 4-(meth)acryloyloxybenzensulfonate, and 3-(meth)acryloyloxypropanesulfonate.

Such acidic group-containing polymerizable monomers may be used singly or in various combinations.

In the acidic group-containing polymerizable monomers described above, it may be preferable to use 10-methacryloyloxydecyldihydrogenphosphate, 6-methacryloyloxyhexyl-3-phosphonoacetate, 4-methacryloyloxyethyltrimellitate and anhydride thereof, 4-acryloyloxyethyltrimellitate and anhydride thereof or the like.

The non-acidic group-containing polymerizable monomer (G) as the polymerizable monomer (C) that can be used for the dental curable composition according to the present invention may be any monofunctional or polyfunctional polymerizable monomer known in the art and commonly used in the dental field that does not contain an acidic group without restriction. Typical examples of the polymerizable monomer generally suitably used include polymerizable monomers having an acryloyl group and/or a methacryloyl group. In the present invention, the terms "(meth)acrylates" and "(meth)acryloyls" are used to comprehensively express both acryloyl group-containing polymerizable monomers and methacryloyl group-containing polymerizable monomers, respectively.

Specific examples of the polymerizable monomer having an acryloyl group and/or a methacryloyl group that can be used as the non-acidic group-containing polymerizable monomer (G) are as follows.

Examples of monofunctional monomers include (meth)acrylic esters such as methyl(meth)acrylate, ethyl(meth)acrylate, butyl(meth)acrylate, hexyl(meth)acrylate, tetrahydrofurfuryl(meth)acrylate, 2-hydroxyethyl(meth)acrylate, glycidyl(meth)acrylate, lauryl(meth)acrylate, cyclohexyl(meth)acrylate, benzyl(meth)acrylate, allyl(meth)acrylate, 2-ethoxyethyl(meth)acrylate, methoxypolyethyleneglycol(meth)acrylate, and glycerol(meth)acrylate, isobornyl(meth)acrylate; silane compounds such as γ-(meth)acryloyloxypropyltrimethoxysilane, and γ-(meth)acryloyloxypropyltriethoxysilane; nitrogen compounds such as 2-(N,N-dimethylamino)ethyl(meth)acrylate, N-methylol(meth)acrylamido, and diacetone(meth)acrylamido.

Examples of bifunctional aromatic monomers include 2,2-bis(4-(meth)acryloyloxyphenyl)propane, 2,2-bis(4-(3-(meth)acryloyloxy-2-hydroxypropoxy)phenyl)propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxyethoxyphenyl)-2-(4-(meth)acryloyloxydiethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxydipropoxyphenyl)propane, 2,2-bis(4-(meth)acryloyloxyisopropoxyphenyl)propane, or the like.

Examples of bifunctional aliphatic monomers include 2-hydroxy-3-acryloyloxypropylmethacrylate, hydroxypivalateneopentylglycol-di(meth)acrylate, ethyleneglycol-di(meth)acrylate, diethyleneglycol di(meth)acrylate, triethyleneglycol-di(meth)acrylate, butyleneglycol-di(meth)acrylate, neopentylglycol-di(meth)acrylate, propyleneglycol-di(meth)acrylate, polyethyleneglycol-di(meth)acrylate, 1,3-butanediol-di(meth)acrylate, 1,4-butanediol-di(meth)acrylate, 1,6-hexanediol-di(meth)acrylate, glycelol-di(meth)acrylate, or the like.

Examples of trifunctional monomers include trimethylolpropane-tri(meth)acrylate, trimethylolethane-tri(meth)acrylate, trimethylolmethane-tri(meth)acrylate, pentaerythritol-tri(meth)acrylate, or the like.

Examples of tetrafunctional monomers include pentaerythritol-tetra(meth)acrylate, ditrimethylolpropane-tetra(meth)acrylate, or the like.

Example of the urethane polymerizable monomer includes bifunctional, trifunctional or more functional di(meth)acrylate having urethane bond or the like. Such di(meth)acrylate is delivered from additional products which consists of polymerizable monomers having a hydroxy group and diisocyanate compounds. The polymerizable monomers described above include 2-hydroxyethyl-(meth)acrylate, 2-hydroxypropyl-(meth)acrylate, and 3-chloro-2-hydroxypropyl-(meth)acrylate; and the diisocyanate compounds described above include methylcyclohexanediisocyanate, methylenebis(4-cyclohexylisocyanate), hexamethylenediisocyanate, trimethylhexamethylenediisocyanate, isophoronediisocyanate, diisocyanatemethylmethylbenzene, and 4,4-diphenylmethanediisocyanate.

Besides the (meth)acrylate polymerizable monomers, an oligomer or a prepolymer having at least one or more polymerizable groups in a molecule may be used without restriction. A substituent such as a fluoro group may be provided in the same molecule.

Such non-acidic group-containing polymerizable monomers may be used singly or in various combinations.

The dental curable composition according to the present invention may contain a hydrophilic polymerizable monomer (H) as a part of the non-acidic group-containing polymerizable monomer (G). If the dental curable composition contains the hydrophilic polymerizable monomer (H), the wettability of the dental curable composition with biological hard tissues (such as enamel and dentin of the natural teeth) as an adherend is improved to increase adhesion.

Herein, polymerizable monomers that resolve in an amount of 10 parts by weight or more in 100 parts by weight of water at 23° C. is defined as hydrophilic polymerizable monomers, and other polymerizable monomers are defined as hydrophobic polymerizable monomers. That is, 10 g of a polymerizable monomer is added to 100 g of water kept at 23° C. in a sample bottle, and the mixture is stirred for 10 minutes to thereafter be left to stand. After the lapse of 10 minutes, the mixture in the sample bottle is observed. If the mixture is resolved uniformly transparently or translucently, the polymerizable monomer is determined as a hydrophilic polymerizable monomer. If not, the polymerizable monomer is determined as a hydrophobic polymerizable monomer.

Specific examples of hydrophilicity polymerizable monomers (H) which can be used for a curable dental composition according to the present invention include, but are not limited to, 2-hydroxyethyl(meth)acrylate, 2-hydroxypropyl (meth)acrylate, 3-hydroxypropyl(meth)acrylate, 1,2-dihydroxypropyl(meth)acrylate, 1,3-dihydroxypropyl(meth)acrylate, 2,3-dihydroxypropyl(meth)acrylate, 2-hydroxypropyl-1,3-di(meth)acrylate, 3-hydroxypropyl-1,2-di(meth)acrylate, pentaerythritoldi(meth)acrylate, 2-trimethylammoniumethyl(meth)acrylchloride, (meth)acrylamide, 2-hydroxyethyl(meth)acrylamide, polyethyleneglycoldi(meth)acrylate (in which the number of oxyethylene groups is more than 9), or the like.

Such hydrophilic polymerizable monomers (G) may be used singly or in various combinations. Among the hydrophilic polymerizable monomers (G), those which resolve in an amount of 20 parts by weight or more in 100 parts by weight of water at 23° C. are preferable, and those which resolve in an amount of 40 parts by weight or more in 100 parts by weight of water at 23° C. are more preferable.

Specific examples of that include 2-hydroxyethyl(meth)acrylate, polyethyleneglycoldi(meth)acrylate (in which the number of oxyethylene groups is 9), polyethyleneglycoldi(meth)acrylate (in which the number of oxyethylene groups is 14), polyethyleneglycoldi(meth)acrylate (in which the number of oxyethylene groups is 23) or the like.

In order for the dental curable composition according to the present invention to be highly wettable with biological hard tissues (such as enamel and dentin of the natural teeth) and express self-adhesion to the tooth substance, the dental curable composition contains the acidic group-containing polymerizable monomer (F) and the non-acidic group-containing polymerizable monomer (G) by a weight ratio of 3:97 to 50:50. In addition, the hydrophilic polymerizable monomer (H) accounts for 5 to 70% by weight of the total of the non-acidic group-containing polymerizable monomer (G).

If the content of the acidic group-containing polymerizable monomer (F) is more than 50 parts by weight, polymerization of other polymerizable monomers may be hindered to adversely affect the physical properties. If the content of the acidic group-containing polymerizable monomer (F) is less than 3 parts by weight, on the other hand, the effect for the self-adhesion to biological hard tissues (such as enamel and dentin of the natural teeth) is not observed.

If the content of the hydrophilic polymerizable monomer (H) in 100 parts by weight of non-acidic group-containing polymerizable monomer (G) is more than 70 parts by weight, polymerization with other polymerizable monomers may be hindered to adversely affect the physical properties. If the content of the hydrophilic polymerizable monomer (H) is less than 5 parts by weight, on the other hand, the wettability of the dental curable composition with biological hard tissues may be poor.

In order to provide the dental curable composition according to the present invention with adhesion to a precious metals, it is also effective for the purpose of the present invention to use a polymerizable monomer containing a sulfur atom in a molecule. Any polymerizable monomer containing a sulfer atom in a molecule may be used irrespective of the type and the number of unsaturated groups, the presence or absence of other functional groups, and so forth.

Specific examples of polymerizable monomers having a sulfur atom which can be used for a curable dental composition according to the present invention include, but are not limited to, (meth)acrylate having a triazinethiol group, (meth)acrylate having a mercapto group, (meth)acrylate having a polysulfide group, (meth)acrylate having a thiophosphate group, (meth)acrylate having a cyclic disulfide group, (meth)acrylate having a mercaptodithiazole group, (meth)acrylate having a thiouracil group, (meth)acrylate having a thiirane group, or the like.

Such polymerizable monomers containing a sulfur atom in a molecule may be used singly or in various combinations.

In order to provide the dental curable composition according to the present invention with adhesion to ceramics, composite resins, and so forth, it is also effective for the purpose of the present invention to use an organosilane compound having at least one polymerizable unsaturated group in a molecule. Any organosilane compound having a polymerizable unsaturated group in a molecule may be used irrespective of the type and the number of unsaturated groups, the presence or absence of other functional groups, and so forth. Such organosilane compounds may be used singly or in various combinations.

Specific examples of organosilane compounds having a polymerizable unsaturated group which can be used for a curable dental composition according to the present invention include, but are not limited to, vinyltrimethoxysilane, vinyltriethoxysilane, vinyltrichlorosilane, vinyl(β-methoxyethoxy)silane, γ-methacryloxypropyltrimethoxysilane, γ-glycidoxypropyltrimethoxysilane, γ-mercaptopropyltrimethoxysilane or the like.

The polymerization catalyst (D) that can be used for the dental curable composition according to the present invention is not specifically limited, and a radical generator known in the art may be used without restriction. In general, the polymerization catalysts are roughly divided into chemical polymerization initiators that are mixed immediately before use to initiate polymerization, thermal polymerization initiators that are heated or warmed to initiate polymerization, and photo polymerization initiators that are irradiated with light to initialize polymerization.

Examples of the chemical polymerization initiators include redox polymerization initiators composed of organic peroxide/amine compound or organic peroxide/amine compound/sulfinate, organic peroxide/amine compound/borate compound, and organic metal polymerization initiators that react with oxygen or water to initiate polymerization. Further, sulfinates and borate compounds may react with a polymerizable monomer having an acidic group to initiate polymerization.

Specific examples of the organic peroxide described above include benzoylperoxide, p-chlorobenzoylperoxide, 2,4-dichlorobenzoylperoxide, acetylperoxide, lauroylperoxide, tert-butylperoxide, cumenehydroperoxide, 2,5-dimethylhexan, 2,5-dihydroperoxide, methylethylketoneperoxide, t-butylperoxybenzoate, or the like.

As the amine compounds described above, secondary amine or tertiary amine having an amine group coupled with an aryl group is preferable. Specific examples of that include p-N,N-dimethyl-toluidine, N,N-dimethylanilline, N-β-hydroxyethyl-anilline, N,N-di(β-hydroxyethyl)-anilline, p-N, N-di(β-hydroxyethyl)-toluidine, N-methyl-anilline, p-N-methyl-toluidine, or the like.

Specific examples of sulfinic acid include sodium benzenesulfinate, lithium benzenesulfinate, p-toluenesulfinate sodium or the like.

Examples of the borate compounds include a sodium salt, a lithium salt, a potassium salt, a magnesium salt, a tetrabutylammonium salt, tetramethylammonium salt or the like, of trialkylphenylboron, trialkyl(p-fluorophenyl)boron, (in which alkyl group is a n-butyl group, a n-octyl group, a n-dodecyl group, or the like).

Examples of the organic metal polymerization initiators include organic boron compounds such as triphenylborane, tributylborane, and partially oxidized tributylborane. As the thermal polymerization initiators to be heated or warmed, azo compounds such as azobisisobutyronitrile, azobisisomethylbutyrate, and azobiscyanovalerate are suitably used besides the organic peroxides described above.

Meanwhile, the photo polymerization initiators may be composed of a photosensitizer, a photosensitizer/photo polymerization promoter, or the like.

Specific examples of the photosensitizer described above include α-diketones such as benzyl, camphorquinone, α-naphthyl, acetonaphthone, p,p'-dimethoxybenzyl, p,p'-dichlorobenzylacetyl, pentanedione, 1,2-phenanthrenequinone, 1,4-phenanthrenequinone, 3,4-phenanthrenequinone, 9,10-phenanthrenequinone, and naphthoquinone; benzoinalkylethers such as benzoin, benzoinmethylether, and benzoinethylether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, and 2,4-diisopropylthioxanthone; benzophenones such as benzophenone, p-chlorobenzophenone, and p-methoxybenzophenone; acylphosphinoxide such as 2,4,6-trimethylbenzoyl-diphenyl-phosphie oxide, and bis(2,6-dimethoxybenzoyl)-2,4,4-trimethylpentylphosphine oxide; α-aminoacetophenone such as 2-benzyl-dimethylamino-1-(4-morpholinophenyl)-butanone-1, 2-benzyl-diethylamino-1-(4-morpholinophenyl)-propanone-1, or the like; ketals such as benzyldimethylketal, benzyldiethylketal, and benzyl(2-methoxyethylketal); titanocene such as bis(cyclopentadienyl)-bis[2,6-difluoro-3-(1-pyrrolyl)phenyl]-titanium, bis(cyclopentadienyl)-bis (pentanefluorophenyl)-titanium, and bis(cyclopentadienyl)-bis(2,3,5,6-tetrafluoro-4-disiloxyphenyl)-titanium.

Specific examples of the photo polymerization promoter include tertiary amines such as N,N-dimethylanilline, N,N-diethylanilline, N,N-di-n-butylanilline, N,N-dibenzylanilline, p-N,N-dimethyl-toluidine, m-N,N-dimethyl-toluidine, p-N,N-diethyl-toluidine, p-bromo-N,N-dimethylanilline, m-chloro-N,N-dimethylanilline, p-dimethylaminobenzaldehyde, p-dimethylaminoacetophenone, p-dimethylaminobenzoate, p-dimethylaminoethylbenzoate, p-dimethylaminoaminobenzoate, N,N-dimetyl-methylanthranilate, N,N-dihydroxyethylanilline, p-N,N-dihydroxyethyl-toluidine, p-dimethylaminophenylalcohol, p-dimethylaminostyrene, N,N-dimethyl-3,5-xylidine, 4-dimethylaminopylidine, N,N-dimetyl-α-naphthylamine, N,N-dimetyl-3-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethylmethacrylate, N,N-diethylaminoethylmethacrylate, and 2,2'-(n-butylimino) diethanol; secondary amines such as N-phenylglycine; barbituric acids such as 5-butyl barbiturate, and 1-benzyl-5-phenylbarbiturate; tin compounds such as dibutyltin-diacetate, dibutyltin-dilaurate, dioctyltin-dilaurate, dioctyltin-diverthatate, dioctyltin-bis(isooctylmercaptoacetate)salt, and tetramethyl-1,3-diacetoxy distannoxane; aldehyde compounds such as laurylaldehyde, and terephthalaldehyde; sulfur containing compounds such as dodecylmercaptan, 2-mercaptobenzoxazole, 1-decanethiol, and thiosalicilic acid.

In order to improve the photo polymerization promotion ability, it is effective to add oxycarboxylic acid such as citric acid, malic acid, tartaric acid, glycodic acid, gluconic acid, α-oxyisobutyric acid, 2-hydroxypropanoic acid, 3-hydroxypropanoic acid, 3-hydroxybutanoic acid, and 4-hydroxybutanoic acid, dimethylolpropionic acid in addition to the photo polymerization promoter described above.

Such radical polymerization initiators may be used singly or in combination of two or more kinds thereof irrespective of the polymerization mode and the polymerization method. The radical polymerization initiator may be subjected to a secondary process, for example, of being encapsulated in a microcapsule as necessary. Among such polymerization initiators, the photo polymerization initiators that are irradiated with light to generate a radical are preferably used, and most suitably used to polymerize a dental curable composition with little air mixed in. Among the photo polymerization initiators, a combination of an α-diketone and a tertiary amine is more preferable, and a combination of a camphorquinone and an aromatic amine in which an amino group is directly bonded to a benzene ring such as p-N,N-dimethylaminoethylbenzoate and an aliphatic amine in which a double bond is provided in a molecule such as N,N-dimethylamino ethylmethacrylate is most preferable. Besides, coumarin, cyanine, and thiazine sensitizing dyes, halometyl group substituted-s-triazine derivatives, photo acid generators that generate a Brønsted acid or a Lewis acid by irradiation with light such as diphenyliodonium salt compounds, quaternary ammonium halides, and transition metal compounds are also used as appropriate according to the use.

The content of the polymerization initiator used in the dental curable composition according to the present invention may be selected as appropriate according to the use, and is preferably in the range of 0.1 to 5 parts by weight, more preferably in the range of 0.1 to 2 parts by weight.

The refractive index (ne) of a cured resin material (E), which is obtained by curing a polymerizable composition containing the polymerizable monomer (C) and the polymerization catalyst (D), is not specifically limited as long as the refractive index (ne) meets the relationship of $0 \leq |na-ne| < 0.01 \leq ne-nb \leq 0.05$ with the refractive index na of the inorganic particle (A) and the refractive index nb of the inorganic particle (B), but is preferably in the range of 1.40 to 1.60, more preferably in the range of 1.45 to 1.55.

If the refractive index (ne) of the cured resin material (E) is less than 1.40, the curability of the dental curable composition may be reduced to cause a problem in mechanical strength. If the refractive index (ne) is more than 1.60, on the other hand, the adhesion of the dental curable composition may be reduced.

While a variety of color expression systems are used in the dental field as a method of measuring and quantifying the color tone of dental materials such as the tooth substance, artificial teeth, porcelain, and hard resins, a contrast ratio defined using a Y value for brightness among three stimulating values or tristimulus values in an XYZ color expression system prescribed according to JIS Z8701 is used as a method of quantifying the opacity of a dental filling material.

The contrast ratio is obtained by placing a disk-shaped specimen of a certain thickness on a standard white background and a standard black background, illuminating the specimen and the background under certain conditions (such as light source and irradiated area), measuring the brightness (Yw) of the white background and the brightness (Yb) of the black background, and calculating the contrast ratio using a specific formula. The contrast ratio is affected by the thickness of the specimen. Thus, the contrast ratio is calculated using the formula (3) provided in "Dental Materials and Appliances Vol. 14, Special Issue 26" (1995), which includes a correction for the thickness of the specimen to obtain a more accurate contrast ratio.

$$\text{Contrast ratio} = 1 - (1 - Yw/Yb)^{1/L} \quad (3)$$

The material is more opaque as the value of the contrast ratio is closer to 1, and more transparent as the value of the contrast ratio is closer to 0.

In the dental curable composition according to the present invention, the refractive index na of the inorganic particle (A), the refractive index nb of the inorganic particle (B), and the refractive index ne of the cured resin material (E), which is obtained by curing a polymerizable composition containing the polymerizable monomer (C) and the polymerization catalyst (D), meet the relationship (2). Thus, the value of the contrast ratio of the dental curable composition according to the present invention after being cured is in the range of 0.3 to 0.7. More preferably, the contrast ratio is in the range of 0.40 to 0.70.

If the contrast ratio of the dental curable composition after being cured is more than 0.7, the transparency of the dental curable composition may be so low as to degrade aesthetics. In addition, the polymerization properties of the dental curable composition may be degraded to reduce adhesion. If the contrast ratio of the dental curable composition after being cured is less than 0.3, on the other hand, the transparency of the dental curable composition may be too high to screen the color of a background such as a cavity wall, which may cause the dental curable composition to be affected by the background color to degrade aesthetics.

Besides the components (A) to (F), components such as an excipient represented by fumed silica, an ultraviolet absorber such as 2-hydroxy-4-methylbenzophenone, a polymerization inhibitor such as hydroquinone, hydroquinone monomethyl ether, and 2,5-ditertiarybutyl-4-methylphenol, a discoloration inhibitor, an antibacterial agent, a coloring pigment, and other additives known in the art may be added as necessary and as desired to the dental curable composition according to the present invention.

Further, water and a solvent miscible with water at a desired ratio may be added as necessary and as desired in consideration of permeability to the tooth substance, decalcification, and biological safety. Examples of the component include alcohols such as methanol, ethanol, and propanol and ketones such as acetone and methylethylketone.

The method of using the dental curable composition according to the present invention is not specifically limited, and the dental curable composition according to the present invention may be used not only singly but also in appropriate combination with other treating materials such as an etching agent, a primer, a bonding material, a self-etching primer, a ceramic primer, a metal primer, and a precious metal primer, bonding materials, and filling/restoring materials.

EXAMPLES

Examples of the present invention will be specifically described below. The present invention is not limited to such examples. The test method to evaluate the performance of dental curable compositions prepared according to the examples and comparative examples is as follows.

(1) Measurement of Average Grain Size of Inorganic Particle

Purpose: to measure the average grain size of the inorganic particle

Method: The average grain size of the inorganic particle was measured in a water solvent using a Microtrac HRA (manufactured by Nikkiso Co., Ltd.) which is a laser-diffraction grain size measuring device. Herein, the term "average grain size" refers to a grain size at which the proportion of the accumulated volume for grain sizes to the volume of the total of particle powder, which is defined as 100%, reaches 50%, and is defined based on the volume.

(2) Measurement of Refractive Index of Inorganic Particle

Purpose: to measure the refractive index of the inorganic particle

Method: Several types of immersion liquids for refractive index measurement having a desired refractive index were prepared in advance using tricresyl-phosphate and dioctyl-adipate (both manufactured by Daihachi Chemical Industry Co., Ltd.). After a small amount of the inorganic particle or an inorganic particle for comparison was placed on a slide glass, several drops of the prepared immersion liquids were dropped. After the mixture was mixed to be uniform, a cover glass was placed to obtain a measurement sample. The measurement sample was placed on a stage of a polarizing microscope (manufactured by Nikon Corporation and having a magnification of 400×) to measure the refractive index (at 23° C.).

(3) Measurement of Refractive Index of Cured Resin Material (E)

Purpose: to measure the refractive index of the cured resin material

Method: Each prepared polymerizable composition was fully injected into a mold (in a shape of a disc having a diameter of 15 mm and a thickness of 1 mm) made of stainless steel. Then, a cover glass was placed on the mold from above, and pressed against the mold using a glass plate. After that, the polymerizable composition was irradiated with light from above the cover glass for 1 minute using a photo polymerization irradiator (Grip Light II manufactured by Shofu Inc.) to be cured. The cured resin material (E) was taken out of the mold to obtain a refractive index specimen. The refractive index specimen was measured using an Abbe refractometer (2T type manufactured by Atago Co., Ltd.) to obtain the refractive index specimen (at 23° C.) of each cured resin material (E).

(4) Measurement of Opacity

Purpose: to evaluate the opacity (contrast ratio) of a cured body of the dental composition Method: Each prepared dental composition was fully injected into a mold (in a shape of a disc having a diameter of 15 mm and a thickness of 1 mm) made of stainless steel. Then, a cover glass was placed on the mold from above, and pressed against the mold using a glass plate. After that, the dental composition was irradiated with light from above the cover glass for 1 minute using a photo polymerization irradiator (Grip Light II manufactured by Shofu Inc.) to be cured. The cured object was taken out of the mold to obtain a specimen. After that, the thickness of the specimen was measured at 5 points using a micrometer, and the average of the thicknesses was determined as the thickness of the specimen.

Each specimen was placed on the background of a standard white background (D65/10° X=81.07, Y=86.15, Z=93.38) and a standard black background (D65/10° X=0.0, Y=0.0, Z=0.0), and illuminated under predetermined constant conditions (light source: C, viewing angle: 20, measurement area: 11 mm) using a color-guide spectrocolorimeter (manufactured by BYK-Chemie GmbH) to measure the brightness (Yw) of the white background and the brightness (Yb) of the black background. The contrast ratio (C) was calculated from the formula (3).

(5) Tooth Substance Adhesion Test

Purpose: to evaluate adhesion of the dental composition to the tooth substance

Method: A narrow piece of a cow tooth was fabricated by extracting a permanent mandibular central incisor from a slaughtered cow, freezing the incisor within 24 hours and unfreezing the incisor, and removing the root portion and cutting away the crown portion. The narrow piece of the cow tooth was embedded in an epoxy resin. The embedded cow tooth was sanded using #600 waterproof abrasive paper to expose enamel or dentin, and then washed with water and dried.

A double-sided tape with a hole having a diameter of 4 mm was affixed to the exposed enamel or dentin to prescribe an adhesion surface. A plastic mold (inside diameter: 4 mm, height: 2 mm) was fixed to the prescribed surface, and the dental composition was injected onto the adhesion surface, and irradiated with light for 20 seconds using a photo polymerization irradiator (Grip Light II manufactured by Shofu Inc.) to be cured. After that, the mold was removed to fabricate an adhesion specimen.

The adhesion specimen was immersed in distilled water at 37° C. for 24 hours. After that, a tooth substance adhesion test was performed for shear bond strength, using an Instron universal testing machine (Instron 5567 manufactured by Instron) at a crosshead speed of 1 mm/min.

[Inorganic Particle]

The refractive index and the average grain size of inorganic particles 1 to 6 used to prepare a dental composition were measured. Table 1 illustrates the results. The inorganic particles were subjected to a silane treatment as appropriate before being used to prepare a dental composition.

TABLE 1

|  | Refractive index | Average grain size (μm) |
|---|---|---|
| Inorganic particle 1 | 1.460 | 0.96 |
| Inorganic particle 2 | 1.490 | 2.88 |
| Inorganic particle 3 | 1.510 | 2.96 |
| Inorganic particle 4 | 1.520 | 7.51 |
| Inorganic particle 5 | 1.530 | 1.21 |
| Inorganic particle 6 | 1.560 | 12.20 |

The materials used to prepare a dental composition are abbreviated as follows.

Bis-GMA: 2,2-bis(4-(3-methacryloyloxy-2-hydroxypropoxy)phenyl)propane
UDMA: 2,2-bis(4-methacryloyloxyethoxyphenyl)propane
HEMA: 2-hydroxyethylmethacrylate
14EG: polyethyleneglycoldimethacrylate (the number of repeating: 14)
CQ: camphorquinone
Tin: dibutyltindilaurate
DMBE: dimethylaminoethylbenzonate
p-TSNa: sodium-p-toluenesulfinate
6-MHPA: (6-methacryloxy)hexylphosphonoacetate
4-MET: 4-methacryloyloxyethyltrimellitate

[Preparation of Polymerizable Composition (I1 to I6) and Measurement of Refractive Index]

Polymerizable compositions (I1 to I6) were prepared according to the compositions indicated in Table 2. In addition, the refractive index of a cured resin material (E) obtained by curing each prepared polymerizable composition (I1 to I6) was measured. Table 2 illustrates the results.

TABLE 2

| | Amount to be compounded (g) | | | | | | | | | | | Refractive index (ne) of cured resin material (E) |
|---|---|---|---|---|---|---|---|---|---|---|---|---|
| | Non-acidic group-containing polymerizable monomer (G) | | Hydrophilic polymerizable monomer (H) | | Acidic group-containing polymerizable monomer (F) | | Polymerization catalyst (D) | | | | | |
| | UDMA | Bis-GMA | HEMA | 14EG | 4-MET | 6-MHPA | CQ | Tin | BHT | p-TS Na | DMBE | |
| I1 | 60.00 | | 30.00 | 10.00 | | 9.00 | 0.30 | 1.50 | 0.10 | | 0.30 | 1.507 |
| I2 | 50.00 | | 50.00 | | | 6.00 | 0.30 | 1.50 | 0.10 | | 0.30 | 1.501 |
| I3 | 30.00 | | 70.00 | | | 4.50 | 0.30 | 1.50 | 0.10 | | 0.30 | 1.495 |
| I4 | | 55.00 | | 45.00 | 5.00 | 9.00 | 0.30 | 1.50 | 0.10 | 0.50 | | 1.539 |
| I5 | | 80.00 | 20.00 | | | 15.00 | 0.30 | 1.50 | 0.10 | | 0.30 | 1.556 |
| I6 | 80.00 | | 20.00 | | 3.00 | 12.00 | 0.30 | 1.50 | 0.10 | | 0.30 | 1.510 |
| I7 | 50.00 | | 10.00 | | | 40.00 | 0.50 | 2.00 | 0.10 | | 0.50 | 1.509 |

[Preparation of Dental Composition]

Dental compositions (compositions 1 to 16) were prepared according to the compositions in Table 3 using the polymerizable compositions indicated in Table 2.

TABLE 3

| | Inorganic particles (A) and (B) (q) | | | | | | Cured resin material (E) (g) | | | | | | |
|---|---|---|---|---|---|---|---|---|---|---|---|---|---|
| | Inorganic particle 1 | Inorganic particle 2 | Inorganic particle 3 | Inorganic particle 4 | Inorganic particle 5 | Inorganic particle 6 | I1 | I2 | I3 | I4 | I5 | I6 | I7 |
| Refractive index | 1.460 | 1.490 | 1.510 | 1.520 | 1.530 | 1.560 | 1.507 | 1.501 | 1.495 | 1.539 | 1.556 | 1.510 | 1.509 |
| Composition 1 | 20 | 64 | | | | | | | 25 | | | | |
| Composition 2 | 20 | | 40 | | | | | | | | | 40 | |
| Composition 3 | 27 | | 7 | | | 60 | | | | | | | |
| Composition 4 | 6.5 | | 58.5 | | | | | 35 | | | | | |
| Composition 5 | | 3 | | | 58.5 | | | | | 35 | | | |
| Composition 6 | 20 | | 50 | | | | | | | | | | 30 |
| Composition 7 | | | 40 | 20 | | | | | | | | 40 | |
| Composition 8 | 55 | | | | | 6.5 | | | | | 40 | | |
| Composition 9 | | 55 | | | | 6.5 | | | | | 40 | | |
| Composition 10 | | | 55 | | | 6.5 | | | | | 40 | | |
| Composition 11 | | | | 55 | | 6.5 | | | | | 40 | | |
| Composition 12 | 9.5 | | | | | 61.5 | | | 32 | | | | |
| Composition 13 | 9.5 | | | | 61.5 | | | | 32 | | | | |
| Composition 14 | 9.5 | 61.5 | | | | | | | 32 | | | | |
| Composition 15 | 45 | 20 | | | | | | | | | 35 | | |
| Composition 16 | 40 | | | | 25 | | | | | | | | 30 |

The dental compositions (compositions 1 to 16) were evaluated as to the adaptability to the formula (4) for the relationship among the respective refractive indexes of the inorganic particles (A) and (B) and the polymerizable composition contained in the dental composition, and assigned as examples and comparative examples. Table 4 illustrates the results.

$$0 \leq |na-ne| < 0.01 \leq ne-nb \leq 0.05 \quad (4)$$

TABLE 4

| | Refractive index | | | | Assignment as |
|---|---|---|---|---|---|
| | Inorganic particle (A) na | Inorganic particle (B) nb | Cured resin material (E) ne | Adaptability to formula (4) | examples and comparative examples |
| Dental composition 1 | 1.490 | 1.460 | 1.495 | ○ | Ex. 1 |
| Dental composition 2 | 1.510 | 1.460 | 1.510 | ○ | Ex. 2 |
| Dental composition 3 | 1.510 | 1.460 | 1.507 | ○ | Ex. 3 |
| Dental composition 4 | 1.510 | 1.460 | 1.501 | ○ | Ex. 4 |
| Dental composition 5 | 1.530 | 1.490 | 1.539 | ○ | Ex. 5 |
| Dental composition 6 | 1.510 | 1.460 | 1.509 | ○ | Ex. 6 |
| Dental composition 7 | 1.520 | 1.510 | 1.510 | x | Comp. Ex. 1 |
| Dental composition 8 | 1.560 | 1.460 | 1.556 | x | Comp. Ex. 2 |
| Dental composition 9 | 1.560 | 1.490 | 1.556 | x | Comp. Ex. 3 |
| Dental composition 10 | 1.560 | 1.520 | 1.556 | ○ | Ex. 7 |
| Dental composition 11 | 1.560 | 1.530 | 1.556 | ○ | Ex. 8 |
| Dental composition 12 | 1.560 | 1.460 | 1.495 | x | Comp. Ex. 4 |
| Dental composition 13 | 1.530 | 1.460 | 1.495 | x | Comp. Ex. 5 |
| Dental composition 14 | 1.490 | 1.460 | 1.495 | ○ | Ex. 9 |

TABLE 4-continued

|  | Refractive index | | | | Assignment as |
|---|---|---|---|---|---|
|  | Inorganic particle (A) na | Inorganic particle (B) nb | Cured resin material (E) ne | Adaptability to formula (4) | examples and comparative examples |
| Dental composition 15 | 1.510 | 1.460 | 1.539 | x | Comp. Ex. 6 |
| Dental composition 16 | 1.560 | 1.460 | 1.510 | x | Comp. Ex. 7 |

The dental compositions according to Examples 1 to 9 and Comparative Examples 1 to 7 were measured for the contrast ratio and the strength of adhesion to dentin. Table 5 illustrates the results.

TABLE 5

|  | Contrast ratio | | |
|---|---|---|---|
|  | Contrast ratio | Adaptability | Strength of adhesion to dentin (MPa) |
| Ex. 1 | 0.56 | ○ | 7.05 |
| Ex. 2 | 0.54 | ○ | 8.19 |
| Ex. 3 | 0.41 | ○ | 7.28 |
| Ex. 4 | 0.37 | ○ | 9.57 |
| Ex. 5 | 0.36 | ○ | 6.78 |
| Ex. 6 | 0.52 | ○ | 7.35 |
| Ex. 7 | 0.69 | ○ | 6.69 |
| Ex. 8 | 0.41 | ○ | 8.37 |
| Ex. 9 | 0.46 | ○ | 6.92 |
| Comp. Ex. 1 | 0.25 | x | 10.72 |
| Comp. Ex. 2 | 0.89 | x | 2.15 |
| Comp. Ex. 3 | 0.72 | x | 3.09 |
| Comp. Ex. 4 | 0.91 | x | 2.58 |
| Comp. Ex. 5 | 0.71 | x | 4.11 |
| Comp. Ex. 6 | 0.77 | x | 4.26 |
| Comp. Ex. 7 | 0.75 | x | 4.65 |

Examples 1 to 9

The dental compositions according to Examples 1 to 9 had a contrast ratio in the range of 0.30 to 0.70, and were found to have moderate opacity suitable for aesthetic restoration. In addition, the dental compositions according to Examples 1 to 9 had a high value of the strength of adhesion to dentin, and thus were found to have good self-adhesion.

Comparative Example 1

The dental compositions according to Comparative Examples 2 to 7 did not meet the relationship (1), and thus were found to have a high contrast ratio and be significantly opaque. Therefore, it is considered that the dental compositions are poor in color tone adaptability to the neighboring tooth substance and thus may not be used for aesthetic restoration. Because the transparency to light was low, the strength of adhesion to dentin was also low.

Comparative Examples 2 to 7

The dental compositions according to Comparative Examples 2 to 7 did not meet the relationship 1, and thus were found to have a high contrast ratio and be significantly opaque. Therefore, it is considered that the dental compositions are poor in color tone adaptability to the neighboring tooth substance and thus may not be used for aesthetic restoration. Because the transparency to light was low, the strength of adhesion to dentin was also low.

While a one-paste dental curable composition has been described above, it is a matter of course that the present invention may also be applied to dental curable compositions obtained by mixing two or more pastes or liquids.

While the preferred embodiment of the invention has been described with a certain degree of particularity with reference to the drawings, obvious modifications and variations are possible in light of the above teachings. It is therefore to be understood that within the scope of the appended claims, the invention may be practiced otherwise than as specifically described.

What is claimed is:

1. A dental curable composition comprising:
an inorganic particle (A) with an average grain size in the range of 0.1 to 50 μm;
an inorganic particle (B) with an average grain size in the range of 0.1 to 50 μm;
a polymerizable monomer (C); and
a polymerization catalyst (D),
wherein:
the refractive index na of the inorganic particle (A) and the refractive index nb of the inorganic particle (B) meet the relationship of na>nb;
the polymerizable monomer (C) contains an acidic group-containing polymerizable monomer (F1) having a phosphonate group and a non-acidic group-containing polymerizable monomer (G) by a weight ratio of F1:G=3:97 to 50:50;
a cured resin material (E), which is obtained by curing a polymerizable composition containing the polymerizable monomer (C) containing the acidic group-containing polymerizable monomer (F1) having a phosphonate group and the polymerization catalyst (D), has a refractive index ne that meets the relationship (1):

$$0 \leq |na-ne| < 0.01 \leq ne-nb \leq 0.05 \quad (1);$$

the acidic group-containing polymerizable monomer (F1) having a phosphonate group is (6-methacryloxy)hexylphosphonoacetate; and
the polymerization catalyst (D) is a photopolymerization initiator.

2. The dental curable composition according to claim 1, wherein the non-acidic group-containing polymerizable monomer (G) contains a hydrophilic polymerizable monomer (H).

3. The dental curable composition according to claim 2, wherein the hydrophilic polymerizable monomer (H) accounts for 5 to 70% by weight of the total of the non-acidic group-containing polymerizable monomer (G).

4. The dental curable composition according to claim 1, wherein the polymerizable monomer (C) further contains an acidic group-containing polymerizable monomer (F2) having acidic groups other than a phosphonate group.

* * * * *